United States Patent [19]

Thompson

[11] 4,090,264
[45] May 23, 1978

[54] LEG PROSTHESIS

[76] Inventor: Johnnie W. Thompson, Rte. 3, Box 263, Pelzer, S.C. 29669

[21] Appl. No.: 745,092

[22] Filed: Nov. 26, 1976

[51] Int. Cl.² .......................... A61F 1/04; A61F 1/08
[52] U.S. Cl. .................................................. 3/27; 3/24; 3/25
[58] Field of Search ........................................ 3/22–30, 3/33, 35, 21, 2

[56] References Cited

U.S. PATENT DOCUMENTS

| 47,353 | 4/1865 | Burr | 3/29 |
| 50,770 | 10/1865 | Lockwood | 3/23 |
| 2,071,711 | 2/1937 | Sprouls | 3/24 |
| 2,667,644 | 2/1954 | Johnson | 3/27 X |
| 2,749,557 | 6/1956 | Riddle | 3/33 |
| 3,969,773 | 7/1976 | Menschik | 3/22 X |

FOREIGN PATENT DOCUMENTS

| 168,889 | 9/1951 | Austria | 3/27 |
| 493,891 | 5/1954 | Italy | 3/25 |

Primary Examiner—Ronald L. Frinks
Attorney, Agent, or Firm—Bailey, Dority & Flint

[57] ABSTRACT

The invention relates to an artificial leg device including a double-jointed knee connection having a pair of tie arms pivotably connected to upper and lower support members and a pair of inner linkage arms pivotably connected to the upper and lower support members intermediate the tie arms. A gear drive assembly is connected between the upper and lower support members providing synchronous rotation therebetween. A ratchet coupling is connected to the gear drive assembly having a pivotable pawl member cooperating with a ratchet wheel to form a lock therebetween for locking the knee joint in a weight-supporting configuration. An operator assembly is carried by the lower support member for operating the pawl and includes an operator rod responsive to pressure on the foot, a resilient biasing means carried by the operator rod, and a quick-release mechanism carried adjacent the upper portion of the operator rod for releasing the resilient biasing means to provide quick and positive disengagement of the pawl from the ratchet.

19 Claims, 9 Drawing Figures

LEG PROSTHESIS

BACKGROUND OF THE INVENTION

This invention relates to a leg prosthesis device having an automatically locking and unlocking knee joint.

Heretofore, several attempts have been made to provide artificial limbs having joints which are automatically locked and unlocked while the wearer is walking. One of the problems encountered with such devices is to insure that the knee joint is positively locked in position when pressure is applied on the leg for supporting the wearer. However, it is necessary that the knee joint automatically unlock as the pressure is removed from the leg during walking so as to permit the wearer to walk in a normal gait. Providing a mechanism which will positively lock and unlock the knee joint without failure is a problem to which considerable attention must be given.

An example of an automatically knee locking device is disclosed in U.S. Pat. No. 2,071,711. In this particular device, it is alleged that the knee joint will be automatically locked in position as pressure is applied to the foot. When pressure is removed from the foot, a spring is utilized for disengaging a dog from the ratchet teeth so as to permit the knee joint to bend. While this particular prosthesis has never been seen by inventor, it would appear that there would be difficulty in controlling the degree of pressure required for locking and unlocking the knee joint during the walking operation.

Another artificial limb which incorporates a knee joint that is automatically locked and unlocked as pressure is applied during walking is disclosed in U.S. Pat. No. 2,943,622.

SUMMARY OF THE INVENTION

It has been found that an improved artificial leg device can be had comprising an upper support member having a first gear element carried thereon and a lower support member. A mechanical knee joint includes a double-joint pivot connection having a pair of linkage arms pivotably connected at a first pivot to the upper support member and at a second pivot to the lower support member. A ratchet coupling is connected to the first gear element having a pivotable pawl member cooperating with a ratchet to form a lock therebetween for locking the knee joint with the upper and lower members in a weight supporting configuration. An operator rod is carried by the support member responsive to pressure on a foot portion of the artificial leg for engaging the pawl with the ratchet. A resilient biasing means is carried by the operator rod. A quick-release mechanism carried adjacent the operator rod is responsive to the movement of the operator rod for aiding in quick disengagement and release of the pawl from said ratchet once pressure is removed from the foot portion permitting natural movement of the leg device during the forward step thereof.

Accordingly, it is an important object of the present invention to provide an artificial limb with a knee joint which is quickly and reliably locked and unlocked during walking.

Another important object of the present invention is to provide an artificial limb with a mechanical knee joint wherein a minimum amount of pressure is required for positively locking the joint in a fixed position.

Another important object of the present invention is to provide a compact knee joint without sacrificing the degree of knee bend flexibility which can be covered in a cosmetically attractive manner.

Still another important object of the present invention is to provide an artificial limb with a knee joint having a double-jointed connection wherein the adjacent leg portions turn in a synchronous manner with each providing an equal portion of the total knee bend providing increased angular knee bend.

These and other objects and advantages of the invention will become apparent upon reference to the following specification, claims and drawings.

DESCRIPTION OF A PREFERRED EMBODIMENT

Figures 1, 2, 3:
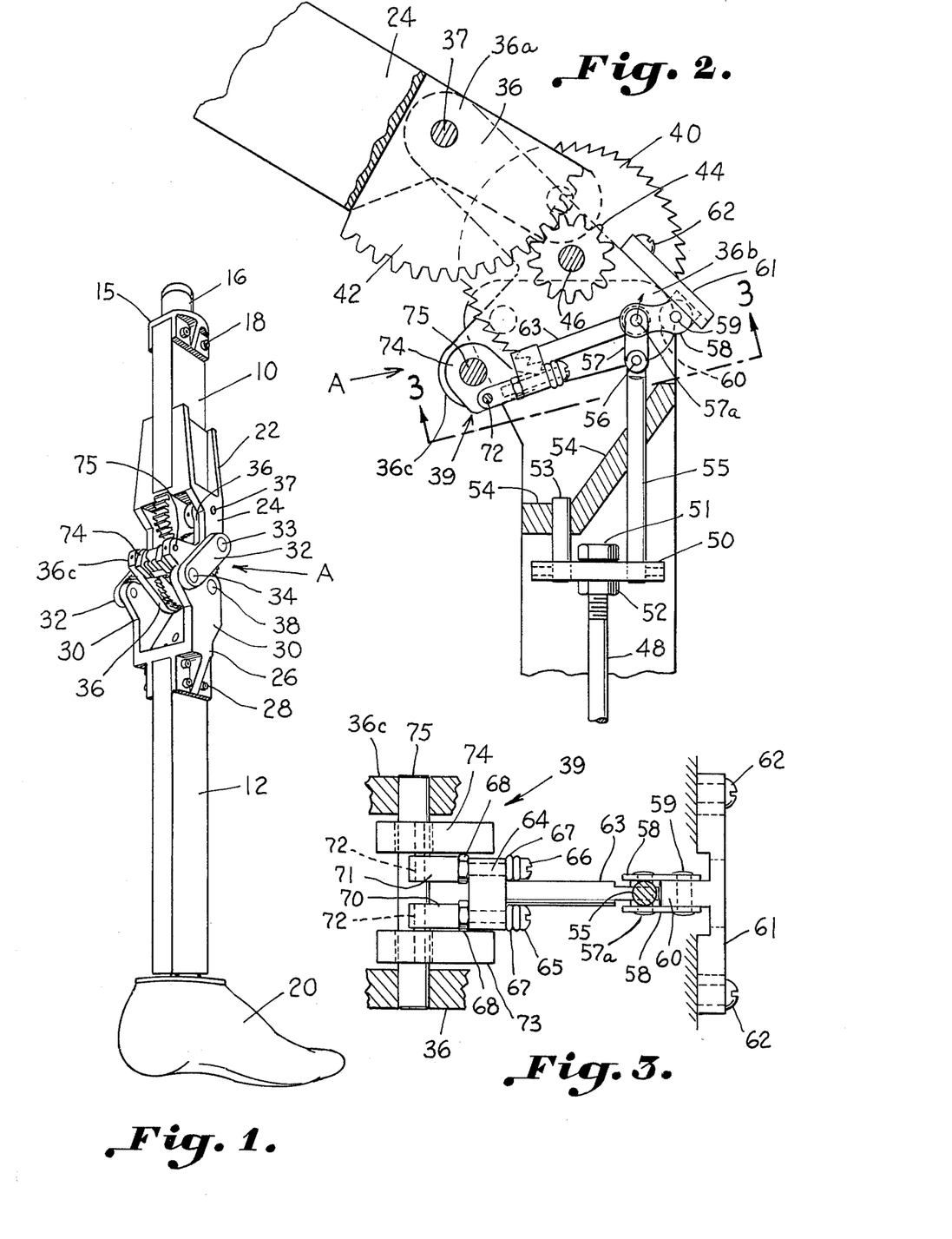
FIG. 1 is a perspective view illustrating a prosthesis construction in accordance with the present invention.
FIG. 2 is an enlarged side elevational view partially in sections illustrating the knee joint of the prosthesis illustrated in FIG. 1.
FIG. 3 is a sectional view taken along line 3—3 of FIG. 2.
Figure 4:
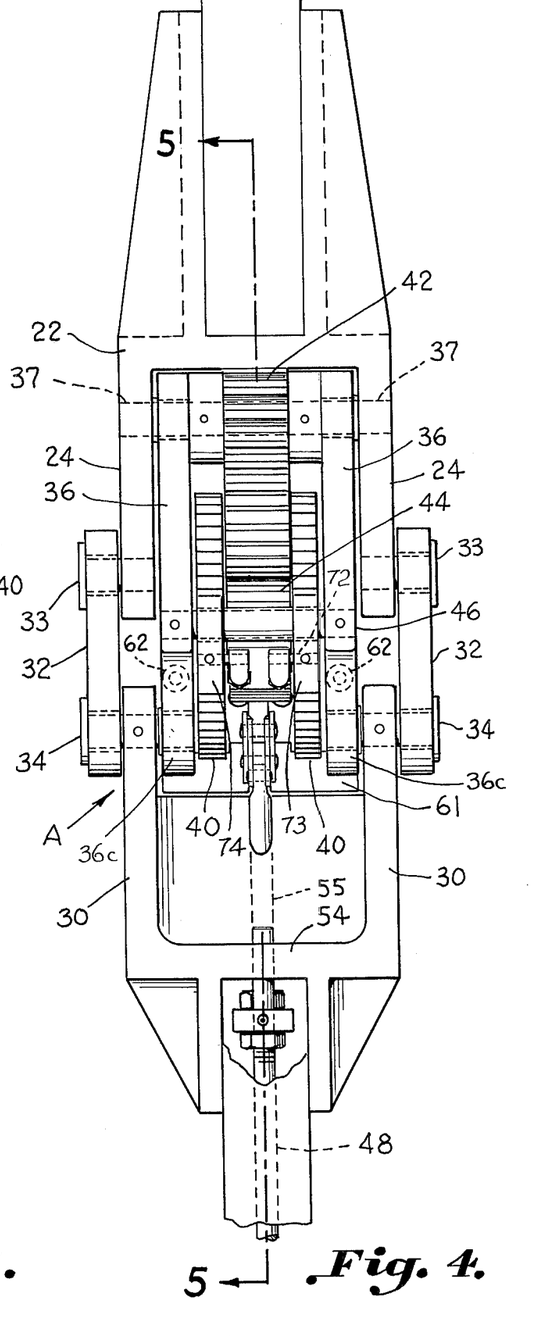
FIG. 4 is an enlarged elevational view taken from the rear of prosthesis illustrating the knee joint.
Figure 5:
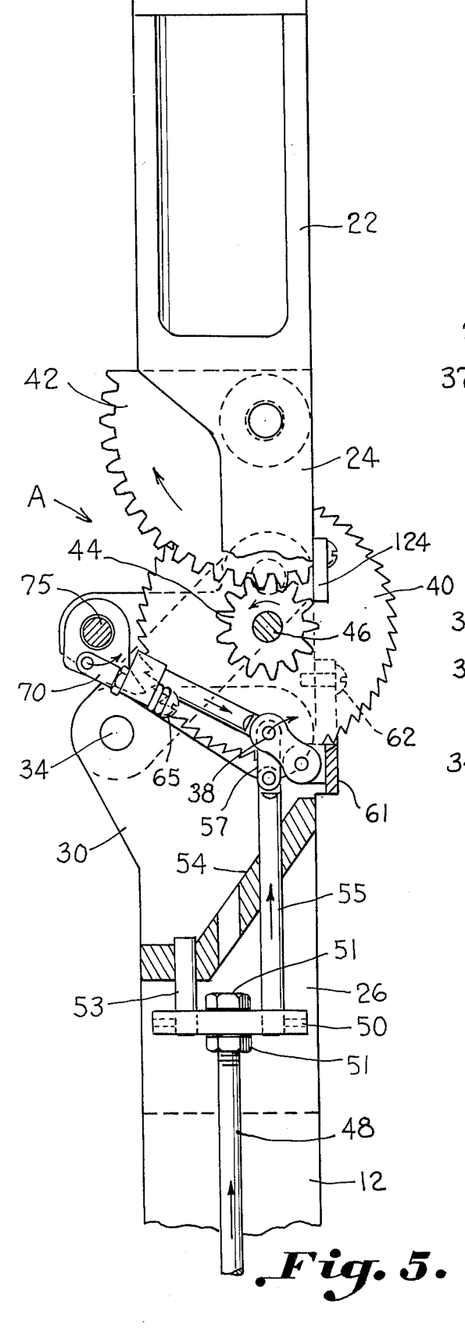
FIG. 5 is a sectional view taken along line 5—5 of FIG. 4 illustrating the pawl operating mechanism for locking and unlocking the knee joint.

Referring in more detail to the drawings, FIG. 1 is a perspective view illustrating a prosthesis constructed in accordance with the present invention which includes an upper supporting member 10 and a lower supporting member 12 which are joined by a mechanical knee joint designated generally at A. Normally positioned on the upper supporting member 10 is a conventional socket or body adapter (not shown) to accommodate the particular user. The vertical extending cylindrical member 16 is secured to the upper end of the upper support 10 as by bolts 18 thereby providing a means upon which a conventional socket or body adapter may be attached to the prosthesis. It is to be understood that any suitable coupling could be utilized in the place of the cylindrical member 16. In order to minimize weight of the prosthesis, the upper and lower members 10 and 12 are constructed of aluminum which provides substantial strength for supporting the user while minimizing the weight of the prosthesis.

Positioned on the bottom of the lower member 12 is a conventional artificial foot 20 which may be secured to the bottom of the lower member 12 through a pivot joint which will be discussed in more detail in connection with FIG. 6. The pivot joint enables the foot to be rotated 90° for permitting the wearer to move the leg through restricted areas such as between automobile seats and the like. Carried on the lower end of the upper member 10 is a bracket 22 which is secured to the upper member 10 by any suitable means such as welding and includes spaced side-walls 24 which extend downwardly approximately half the distance through the knee joint A. The lower member 12 also includes a bracket 26 mounted on the upper end thereof as by bolts 28 having spaced upwardly extending side-walls 30. The walls 30 terminate directly below the downwardly extending walls 24 of the upper bracket.

A pair of outer linkage tie arms 32 pivotably connect the upper bracket 22 to the lower bracket 26. The linkage tie arms 32 are connected by means of a pivot joint 33 to the upper bracket and by means of a pivot joint 34 to the lower bracket. The tie arms 32 maintain the upper and lower members 10 and 12, at substantially the same angle of bend relative to the knee joint A during bending thereof.

A pair of inner linkage arms 36 also pivotably connect the side walls 24 and 30 of the upper and lower members 22 and 26 together. As seen in FIG. 2, the inner linkage arm 36 is substantially dog-leg or "L" shaped. An upstanding protrusion 36a of the inner linkage arm 36 is pivotably secured at pivot 37 to the side wall 24. An intermediate portion of the inner linkage arm 36b is pivotably secured to the wall 30 of the bracket member 26 by pivot 38. A rearwardly extending portion 36c of the inner linkage arm 36 is provided for pivotably supporting a pawl assembly, generally designated by the reference character 39, which cooperates with a ratchet gear 40 for locking the knee joint in a weight-supporting position.

When the knee joint is flexed or bent, a gear drive assembly is provided for permitting the upper member 22 to pivot relative to the lower member 12 in a smooth synchronous manner. This is accomplished through a pair of gears. An upper gear 42 which spans approximately 90° is secured to a lower surface of the upper member 22 between the side walls 24 by any suitable means such as bolts, not shown. Meshed with this drive gear 42 is a small spur gear 44 which is journaled on a shaft 46 extending between the side walls of the inner linkage arms 36. The spur gear is in turn, keyed to the ratchet gear 40 by means (not shown) so that gears 40 and 44 rotate together. Therefore, as the wearer walks and the knee joint bends, the drive gear 42 rotates the spur gear 44 and, in turn, the ratchet gear 40. This permits uniform and controlled movement between the upper portion of the leg 10 and the lower portion of the leg 12 during walking.

In order to insure that the leg is locked in position when pressure is applied to the foot when walking, the pawl assembly 39 is utilized for engaging the ratchet wheel 40. Thus, the assembly of ratchet 40 and pawl 39 provide a ratchet coupling connected to the gear 44 for locking the drive gears 42 and 44 against relative rotation when weight is placed on the leg. The ratchet-pawl assembly is operated through a vertically extending operator rod or linkage 48 which is coupled to a horizontal plate 50 provided in the lower member 12 by means of space nuts 51 and 52 threaded on the upper end of linkage 48. A guide rod 53 extends upwardly from the horizontal plate 50 through a hole provided in a wall 54 forming a part of the bracket 26. On the other end of the plate 50 is a vertically extending linkage arm 55 which extends through a hole provided in the incline portion of wall 54 as provided for transferring movement from the linkage 48 to the pawl assembly 39.

The upper end of the linkage arm 55 is pivotably connected at 56 to a lower end of a small link 57. The upper end of the link, 57 is pivotably connected at 57a between a pair of spaced plates 58 which are best illustrated in FIG. 3.

The other end of the spaced plates 58 are pivotably connected by a pin 59 extending through a protrusion 60 extending inwardly from a plate 61. The plate 61 is secured by means of screws 62 to the front edges of the spaced inner linkage arms 36. A pawl actuator rod 63 has one end connected to the pivot pin 57a through which linkage arms 58 and also the linkage 57 are pivoted on. The other end of the pawl actuator rod 63 is threaded in an upper portion of block 64 so that such can be adjusted. Carried in the lower end of the block 64 are a pair of screws 65 and 66 which have a pair of rubber O-rings 67 provided adjacent to the head thereof. The purpose of the O-rings 67 will be made apparent during the description of the operation of the prosthesis. Positioned on the other end of screws 65 and 66 are locking nuts 68. The ends of the screws 65 and 66 are threaded into pawl operator blocks 70 and 71 which are pivoted on one end of a pin 72. The other end of the pins 72 are fixed to pawls 73 and 74. The pawls themselves are pivotably secured on shaft 75 extending between the inner linkage arms at 36c.

In operation, as the wearer places the foot 20 on the ground, the pressure exerted thereagainst forces the rod 48 upwardly. This force is transferred through linkage arm 55, linkage 57, pivoting the linkage arm 58 upwardly about pivot point 59. As the linkage 58 is pivoted about pivot 59 it pulls the pawl actuator rod 63 forward causing the pawls 73 and 74 to pivot about shaft 75 to engage the ratchet gear 40. The force is imparted through the actuator rod 63, the block 64, screws 65 and 66, O-rings 67, pawl operator blocks 70 and 71, and pins 72. The screws 65 and 66 can be adjusted so that the pawls 73 and 74 can engage the ratchet gear 40 at a slightly different time. The ratchet gear wheels 40 are positioned on the shaft 46 so that their ratchet teeth are offset increasing the number of locking positions for the pawl members. For example, pawl 73 may engage the teeth of ratchet gear 40 approximately ½ pitch of a tooth prior to pawl 74 locking the knee joint at more precise increments.

The pin 72 extending through the operator block 70 is fixed to the pawl 73 for causing the pawl to pivot about the shaft 75 when the operator block 70 is manipulated. Pawl 74 is likewise affixed on pin 72 journaled in block 71. It is also noted that the pawl has a sharpened point 73a which corresponds substantially to the pitch of the teeth on ratchet wheel for engaging therein. The inner end of the pawl has a slight radius thereon so that such can be readily inserted and removed from the teeth of the ratchet wheel 40.

Figure 8:
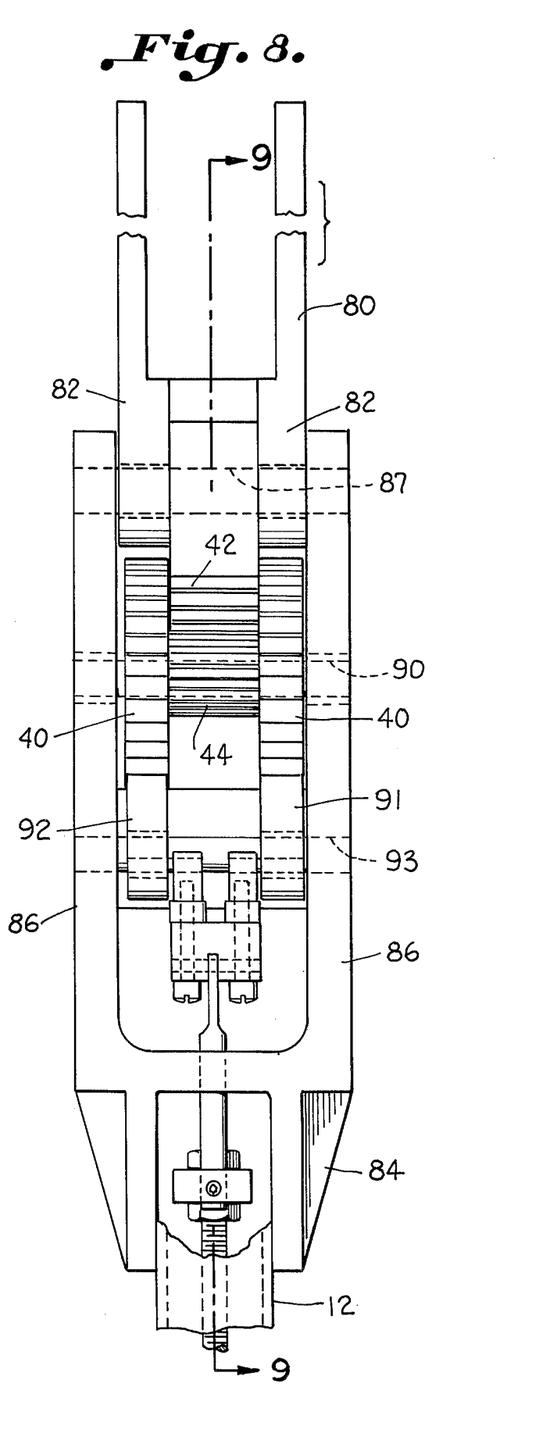
FIG. 8 is a rear elevational view illustrating the knee joint of a modified form of the invention.
Figure 9:
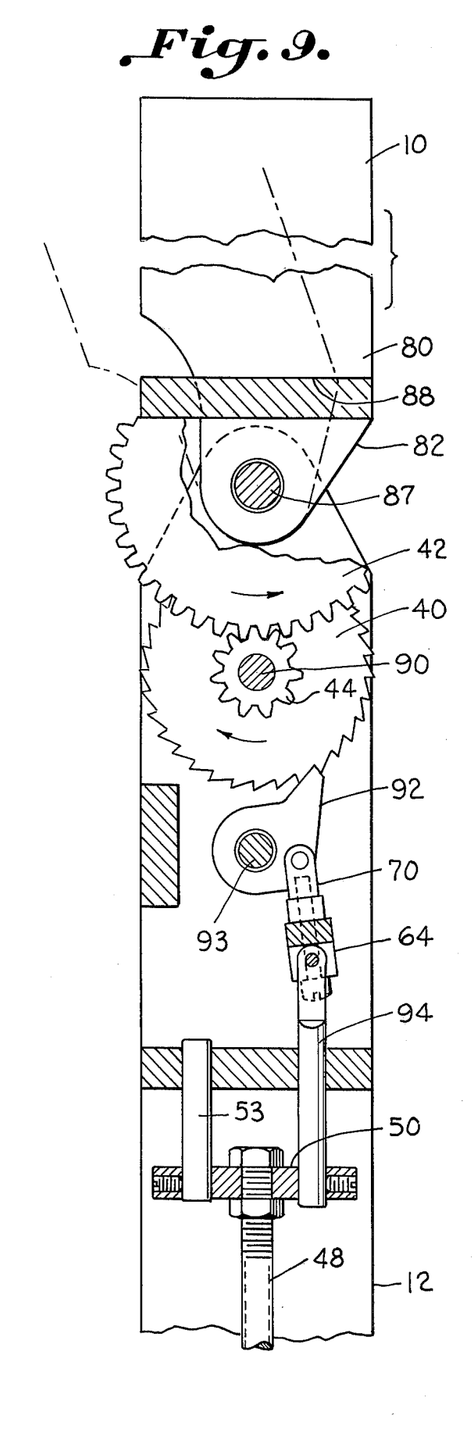
FIG. 9 is a sectional view taken along line 9—9 of FIG. 8.

Referring now in more detail to FIGS. 8 and 9 as illustrated, a modified form of the invention wherein a single pivot is utilized as compared to the double pivot point of FIGS. 1 through 7. The double pivot construction of FIGS. 1 through 7 is normally more suitable for heavier wearers and provides greater flexibility, however, if it is desired to reduce the weight of the legs still further, a single pivot single joint knee such as illustrated in FIGS. 8 and 9 could be utilized. One problem with the joint illustrated in FIGS. 8 and 9 is that the degree of bending the joint is limited as compared to the joint of FIGS. 1 through 7. In the device illustrated in FIGS. 8 and 9, the amount of degree of bend would be limited to approximately 90°.

Like reference characters will be used for corresponding components of the device illustrated in FIGS. 8 and 9. The drive gear 42 of the device illustrated in FIG. 1 spans approximately 180°.

Referring in more detail to FIG. 9, a bracket 80 is carried on the lower end of the upper member 10 and includes a pair of space side walls 82 which extend into the knee joint. Positioned on the upper end of the lower leg 12 is a bracket 84 which also has a pair of space side walls 86 which are pivotably joined to the spaced side walls 82 by means of a rod 87. The drive gear 42 is secured to a plate 88 carried between the space side walls 82 of the upper bracket 80. The spur gear 44 is journaled on a shaft 90 which is fixed to the side walls 86 of the lower member 84. The ratchet wheels 40 are carried on opposite sides of the spur gear 44 and are secured thereto by keying, not shown.

The pawl arrangement for locking the knee joint by engaging the ratchet gears 40 includes a pair of pawls 91 and 92 which are pivotally secured on shaft 93 extending between the side walls 86. A pawl operator rod 94 extends form the block 50 carried in the member to block 64 for manipulating the pawls 91 and 92. The block 64 has screws extending therethrough which are, in turn, connected to pawl operator block 70 for operating the pawl in identical manner as described previously in connection with the embodiment illustrated in FIGS. 1 through 7.

In operation of the device illustrated in FIGS. 8 and 9 as the user places his foot on the ground, pressure is exerted upwardly on the rod 48 causing the pawl operator rod 94 to be forced upwardly. This, in turn, causes the pawls 91 and 92 to engage the ratchet wheels 40 for locking the knee joint in a fixed position. As the user lifts his foot on the ground such, in turn, causes the rod 48 to be shifted downwardly, the pawl disengages from the ratchet wheels 40 to permit the knee to bend. As the leg is swung forward in the walking movement, the upper portion of the leg stops and the lower portion continues until the foot is again placed on the ground causing a pressure to be exerted upwardly on the rod 48 to lock the pawl in engagement with the ratchet wheel 40, so that the user can place his weight on the leg.

Figures 6, 7:
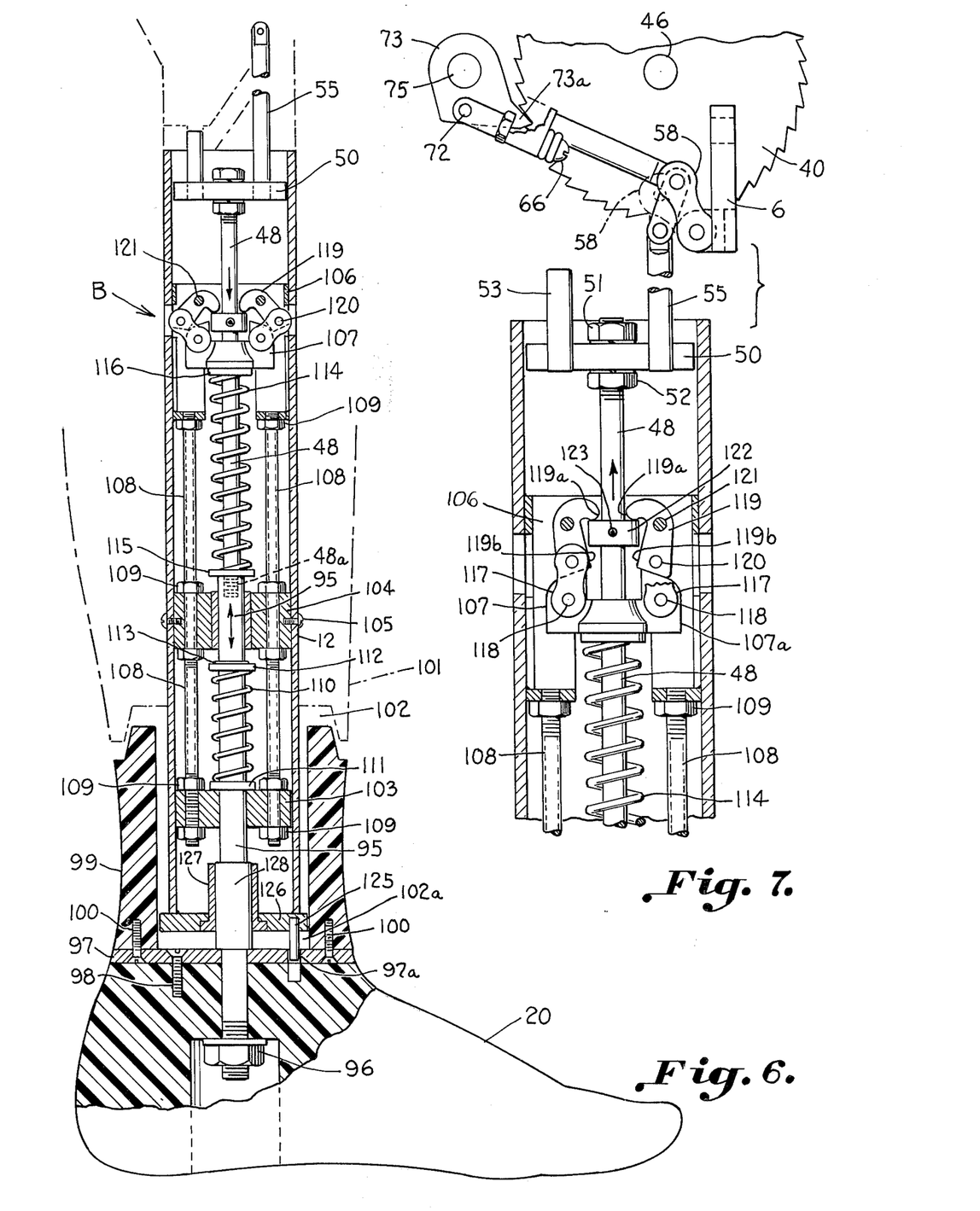
FIG. 6 is an enlarged elevational view partially in section illustrating the mechanism carried in the lower portion of the leg to which forces are transferred for locking and unlocking the knee joint.
FIG. 7 is an enlarged fragmentary side elevational view illustrating the connection between the mechanism carried in the lower portion of the leg and the couplings provided in the knee joint.

Referring now to FIGS. 6 and 7, the lower support member 12 is shown in detail which includes a ratchet unlocking assembly B for ensuring that the pawls 73 and 74 are disengaged from the ratchet wheel 40 once body weight and pressure is removed from the artificial leg member permitting a natural upswing thereof. The ratchet unlocking assembly B includes an elongated bolt member 95 which is made intergral with a remote end 48a of shaft 48. The shaft 48 may be affixed to the elongated bolt member 95 by providing a threaded end at 48a which is received in an internal threaded opening formed in 95. The opposing end of elongated bolt member 95 is secured to an artificial foot member 20 by a suitable washer and nut means 96. The shaft 48 and rod 95 comprise a pawl operator rod for operating pawls 73 and 74.

Mounted on the artificial foot member 20 is a plate 97 attached by a screw 98. The plate member 97 is, in turn, affixed to an exterior artificial ankle portion 99 by means of screws 100. The remaining exterior portion of the lower support member 12 is formed in any conventional manner and is secured to the upper support member 10 adjacent the knee joint A in a cooperating manner with a suitable knee covering. A space 102 is formed between the ankle portion 99 and an exterior leg cover portion 101, which covers lower support 12, for allowing upward movement of the artificial foot 20 and ankle 99 as will be discussed more fully hereinafter.

The ratchet unlocking assembly B is housed completely within the interior of the lower support member 12 and further includes a block member 103 through which the bolt member 95 is slidably received affixed to a second block member 104. The block member 104, through which the bolt member 95 also slides, is affixed to the lower support member 12 by any suitable means such as metal screws 105.

An upper housing member 106 is provided adjacent to the upper portion of the lower support member 12 for housing a ratchet disengaging member 107. The housing member 106 is attached to the block member 104 by a pair of threaded bolt members 108. The threaded bolt members 108 are preferably one-piece bolt members which extend through the block 104 and are attached to the block member 103. The threaded bolt members 108 provide for adjustable spacing between the block members 103 and 104 and the housing member 106. This adjustable spacing also adjusts the spring tension. The threaded bolt members 108 are provided with nut members 109 adjacent each block member and base member for positioning each member relative to the threaded bolt members 108.

A first spring member 110 is carried on the bolt member 95 between a pair of spaced washer members 111 and 112 slidably carried on the bolt 95. A spring lock ring 113 is carried adjacent to washer 112 so that the washer moves downward with the bolt 95 to compress spring 110.

A second spring member 114 is carried between washers 115 and 116 on shaft member 48. The washer 115 is carried on the enlarged end of bolt member 95 so that it moves upwardly therewith causing spring 114 to be compressed. Washer 116 is carried against ratchet disengaging member 107 and is slidably carried over the shaft 48.

The ratchet disengaging member 107 provides a quick-release mechanism for the ratchet and pawl and includes a base 107a through which the shaft 48 extends. The ratchet disengaging member 107 further includes a pair of linkage members 117 pivotably carried about pivot 118 on each side of the base 107a. The rear linkages 117 are directly behind the front linkages shown in FIG. 7 and cannot be seen. A cam member 119 is pivotably carried by a movable pivot 120 between each front and rear pair of linkage members 117. The cam member 119 includes a cam finger portion 119a pivotably carried about a second fixed pivot 121 which is affixed to the housing member 106.

A collar member 122 is carried on the pawl operator shaft 48 and provides an abutment member thereon. The collar member 122 is affixed to shaft 48 by a set screw 123 and may be adjustably positioned on the shaft 48.

In operation, when downward pressure is exerted on the artificial leg member, the artificial foot 20 and ankle portion 99 will move upwardly causing the elongated bolt member 95 to move upwardly so as to close the space 102 and 102a. As the bolt member 95 is moved upwardly, the spring 114 will be compressed from both ends and shaft 48 will also be moved upwardly in accordance with the movement of bolt 95. After the shafts 95 and 48 have moved a very short distance upwardly, one of the pawls 73 or 74 will engage the ratchet wheel 40, and the cam finger portion 119a will be engaged by collar 122, locking the pawl in engagement. The flexible "O" ring 67 allows separation at this moment between locking nut 68 and block 64, which is caused by the off-set in the teeth of ratcher gear 40, thus allowing shaft 95 and 48 to continue upwardly closing the space at 102 and 102a. Collar 122 accordingly moves simultaneously with shaft 95 and 48 and produces a rotation of cam finger 119 at 119a about pivot 121 which produces an inward movement of the linkage 117 and a downward thrust of disengaging member 107 through pivots 120 and 118. In this position, the artificial leg member, including the upper and lower support members is ready for supporting the weight of the wearer so that a step forward may be taken off of the artificial leg as a base. During this operation, the ratchet and pawl will be engaged and the pawl disengaging member 107 will be in a locked position as shown in FIG. 7 wherein collar member 122 is locked between a cam finger portion 119a and protruberant base portion 119b.

Once the artificial leg has been used as a support for taking a forward step and the wearer's weight has once again been shifted to the natural leg, it is necessary that the pawl 73 be disengaged from the ratchet wheel 40 as quickly and reliably as possible to prevent the appearance of a stiff-legged gait on the upswing of the artificial leg. As the artificial leg is swung forward, the pawl member normally experiences some backlash of the ratchet teeth tending to hold or lock the pawl in place. This action opposes quick pawl/ratchet disengagement producing an unnatural gait in prior artificial leg devices, and can prevent disengagement altogether.

To disengage the ratchet quickly and positively once the pressure has been taken off the artificial foot member 20, the collar member 122 will move downwardly due to compression from the spring 114 and the shaft member 95 is moved downwardly accordingly. As the collar member moves downwardly, it engages the protuberant base portion 119b pivoting the cam members 119 and the linkage members 117 outwardly about pivots 118 and 121, respectively. The outward movement of linkages 117 and the cam member 119 releases the ratchet disengaging member 107 from the position as shown in FIG. 7. This allows the compression of spring 114 to be released from both ends of the spring substantially simultaneously permitting quick disengagement of the pawls 73 and 74.

Following pawl and ratchet disengagement and as the upswing of the artificial leg is begun, a slight forward body movement by the wearer produces a movement of the upper support member 10 as shown in FIG. 2. This movement of the upper support member will cause the gear 42 to rotate slightly in a clockwise direction causing the spur gear 44 to rotate in a counterclockwise direction. The counter-clockwise rotation of the gear 44 will cause the ratchet wheel 40 to rotate in a counter-clockwise direction allowing a number of the ratchet teeth to pass by the pawl 73. The ratchet wheel 40 will turn past the pawl 73 during the momentum created by the body motion until at such time as the lower member 12 overcomes and reverses the said action such that the lower member 12 and upper leg member 10 are aligned in such a relationship that the spur gear 44 abuts an abutment in the form of a stop member 124 carried by the outer member 24 of the upper leg member 10. At this time pressure on the foot 20 will lock the artificial leg in the straightened position. However, in the event the wearer should need the support of the artificial leg during any moment of the step carrying through, he need only to apply pressure to the foot locking the knee joint as just described herein.

The clearance provided by spaces 102 and 102a is needed to accomodate this quick downward movement of rod 95 and the released downward biasing force of spring 114. On the other hand, it is desirable that only slight pressure on foot portion 20 be required to engage pawl 73 or 74. To satisfy this requirement the linkage assembly for engaging the pawls, namely 57, 58, 63 and blocks 64, 70, and 71, is designed to engage the pawls after rod 48 has traveled only one-thirty seconds of an inch upwards. Since rod 48 will move approximately one-fourth of an inch when space 102a is closed completely, resilient O-rings 67 will accommodate the additional upward travel of linkage 57 and pivot 57a. That is, block 64 will compress O-rings 67 to permit this further upward movement. This action also insures that the pawls are tightly engaged in the ratchet teeth and that one of the pawls is engaged in the offset ratchet wheels. However, the additional upward travel is not such as to allow both pawls 73 and 74 to engage.

In order that the wearer be enabled to turn his ankle and foot so as to pass through restricted areas, a locking pin member 125 is provided having one end affixed to a plate 126 which slidably receives a collar 128 carried on the bolt, member 95 for aligning the bolt and ensuring that the bolt member moves in linear alignment. In the event that the user of the artificial leg wishes to turn the ankle and foot portions, he merely pushes the foot portion 20 downwardly disengaging the locking pin 125 from an opening 97a formed in the foot plate 97 releasing the foot for rotation. The spring 110 would be under compression during this operation and would allow for the locked pin 125 to be received again in the opening 97a once the artificial foot 20 is returned to its orignal position. The opening 97a extends into the foot portion 20 so as to allow the lock pin 125 to penetrate deeply into the foot during pawl engagement operations as the space 102a is closed.

Thus, it can be seen that an advantageous artificial leg device can be had in accordance with the present invention wherein the double-joint knee connection can bend approximately 180° or more depending on the length of inner linkage arms 36. The lower support member of the leg device provides approximately one-half of the knee pivot while the upper support member provides the other half of the knee pivot. The more compact construction of the double-joint pivot provides a knee joint which is more easily covered to appear as a natural knee joint. The quick-release mechanism provides positive locking of the knee joint during weight support while providing quick and reliable unlocking of the knee joint during the forward movement of the artificial leg.

While a preferred embodiment of the invention has been described using specific terms, such description is for illustrative purposes only, and it is to be understood that changes and variations may be made without departing from the spirit or scope of the following claims.

What is claimed is:

1. In an artificial leg device having an upper support member, a lower support member, a mechanical knee joint connected between said upper and lower support members, locking means carried by said lower support member for locking said upper and lower support members in a locked position to support the weight of the wearer, the improvement comprising:

(a) said knee joint having a double-joint pivot connection connected between said upper and lower support members comprising:

(i) a pair of linkage arms pivotably connected at a first pivot to said upper support member and at a second pivot to said lower support member, (ii) gear drives means connected between said upper and lower support members permitting said upper support member to turn about said first pivot while said lower support member turns about said second pivot providing smooth synchronous motion therebetween and increased knee bend flexibility, and (iii) a pair of tie arms pivotably connected to said upper and lower support members for maintaining said upper and lower supports at substantially the same angle relative to the knee joint connection during bending of the knee.

2. The apparatus set forth in claim 1 wherein said gear drive means includes a first gear element carried on said upper support member and a second gear element carried intermediate said linkage arms in meshing relationship with said first gear element, and said locking means includes a ratchet coupling carried by said lower support member connected to said second gear element.

3. The apparatus set forth in claim 2 wherein each said linkage arm includes an upstanding arm portion connected at said first pivot, an intermediate arm portion connected at said second pivot, and an extended arm portion extended rearwardly from said intermediate portion.

4. The apparatus as set forth in claim 2 wherein said ratchet coupling includes a ratchet wheel carried coaxially on each side of said second gear element, pawl means carried adjacent said ratchet wheels for engaging said ratchet wheels to provide a lock therebetween, said ratchet wheels having offset ratchet teeth relative to each other providing an increased number of incremental locking positions for more positive engagement of said pawl means with said ratchet wheels.

5. The apparatus set forth in claim 2 wherein said locking means further includes an abutment carried by said upper support member, said second gear element abutting said abutment when said upper and lower support members are in said locking position.

6. An artificial leg device having an upper support member, a gear element carried on said upper support member, a lower support, a mechanical knee joint connecting said upper and lower support members, and a ratchet coupling connected to said gear element including a pawl member carried by said lower support member for locking said knee joint with said upper and lower support members in a weight supporting configuration, a pawl operator mechanism comprising:

an operator rod carried by said lower support member responsive to pressure on a foot portion for engaging said pawl with said ratchet coupling;

a quick-release mechanism carried adjacent said operator rod for disengaging and releasing said pawl from said ratchet once pressure is relieved from said operator rod;

resilient biasing means carried by said operator rod;

said quick-release mechanism including a cam member being movable to a locked position by said operator rod as said pawl and ratchet engage to lock said pawl in engagement with said ratchet while locking said resilient means in a biasing condition;

said cam member being releasable from said locked position in response to removal of said pressure to aid in the quick release of said resilient means from said biasing condition;

said released resilient means exerting a force on said operator rod to disengage said pawl from said ratchet ensuring quick and positive disengagement thereof.

7. The apparatus set forth in claim 6 wherein said quick-release mechanism includes an abutment member carried by said operator rod; said abutment member engaging said cam member in response to said pressure being exerted on said foot portion pivoting said cam member to said locked position.

8. The apparatus set forth in claim 6 wherein said cam member includes a cam finger portion pivotable about a fixed pivot and a protuberant base portion pivotably carried by a movable pivot, said operator rod including an abutment member initially engaging said cam finger portion in response to upward movement of said operator rod pivoting said base portion inwardly toward said rod locking said abutment member between said finger portion and base portion of said cam member to lock said pawl in engagement.

9. The apparatus set forth in claim 8 wherein said cam member and hence said operator rod are released by said abutment engaging said base portion following removal of pressure from said foot portion causing said base portion to pivot outwardly.

10. An artificial leg device comprising:

an upper support member having a first gear element carried thereon;

a lower support member;

a mechanical knee joint having a double-joint pivot connection including a pair of linkage arms pivotably connected at a first pivot to said upper support member and at a second pivot to said lower support member;

a ratchet coupling connected to said first gear element having a pivotable pawl member cooperating with a ratchet to form a lock therebetween for locking said knee joint with said upper and lower members in a weight supporting configuration;

an operator rod carried by said support member responsive to pressure on a foot portion of said artificial leg for engaging said pawl with said ratchet;

a resilient biasing means carried by said operator rod;

a quick-release mechanism carried adjacent said operator rod responsive to the movement of said operator rod for aiding in quick disengagement and release of said pawl from said ratchet once pressure is removed from said foot portion permitting natural movement of said leg device during the forward step thereof.

11. The apparatus set forth in claim 10 further comprising pair of tie arms pivotably connected to said upper and lower support members for maintaining upper and lower support at essentially the same angle relative to the knee joint connection during bending of the knee.

12. The apparatus set forth in claim 10 wherein said ratchet coupling includes a second gear element carried intermediate said pair of linkage arms in meshing relationship with said first gear element, a ratchet wheel carried coaxially with said second gear element adjacent each side thereof, said ratchet wheels having offset teeth relative to each other for permitting an increased number of incremental locking positions for said pawl member.

13. The apparatus set forth in claim 12 further including an abutment carried by said upper support member, said second gear element abutting said abutment when said upper and lower members are in a straightened configuration.

14. The apparatus set forth in claim 10 wherein said foot portion is pivotable about said lower support member.

15. The apparatus set forth in claim 14 further comprising:
a lockpin member carried adjacent a bottom end of said lower support member;
a recess means formed in said foot portion for receiving said lockpin member;
biasing means urging said lockpin member into said recess; and
said foot portion being movable to overcome said biasing means so as to release said lockpin member from said recess permitting pivoting of said foot portion about said support member.

16. The apparatus set forth in claim 10 wherein said quick-release mechanism is locked in a first position when said pawl and ratchet are engaged locking said resilient means in a biasing condition, said quick-release mechanism having a second position following removal of pressure from said foot portion to release said resilient means from the biasing condition so that said resilient means exerts a force on said operator rod to disengage said pawl from said ratchet insuring quick and positive disengagement thereof.

17. The apparatus set forth in claim 3 wherein said ratchet coupling includes at least one ratchet wheel carried co-axially with said second gear element and a pawl assembly carried between said rearwardly extended arm portions adjacent a distal end thereof having a pivotable pawl for engaging said ratchet wheel in said locked position.

18. The apparatus set forth in claim 17 further including an operator rod carried by said lower support member responsive to pressure on an artificial foot portion for operating said pawl member and wherein said pawl assembly includes a pair of pawl members pivotably carried between said extended arm portions and adjustable actuator means connected between said pawl members and said operator rod for independently adjusting the pivoting position of said pawl members relative to each other so as to engage said ratchet wheels at offset positions providing an increased number of incremental locking positions.

19. The apparatus of claim 6 further comprising actuator means connected between said operator rod and said pawl member having a resilient member permitting further movement of said operator rod in an upward direction following pawl/ratchet engagement and providing a distance for greater downward displacement of said operator rod when acted upon by said released resilient biasing means for pawl/ratchet disengagement.

* * * * *